(12) United States Patent
Tanino et al.

(10) Patent No.: US 10,087,129 B2
(45) Date of Patent: Oct. 2, 2018

(54) METHOD FOR PRODUCING CYCLIC DIKETONE COMPOUND

(71) Applicant: Kao Corporation, Tokyo (JP)

(72) Inventors: Kenji Tanino, Wakayama (JP); Daichi Sakoda, Wakayama (JP); Shu Sakamoto, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/533,251

(22) PCT Filed: Dec. 22, 2015

(86) PCT No.: PCT/JP2015/085772
§ 371 (c)(1),
(2) Date: Jun. 5, 2017

(87) PCT Pub. No.: WO2016/104474
PCT Pub. Date: Jun. 30, 2016

(65) Prior Publication Data
US 2017/0362153 A1 Dec. 21, 2017

(30) Foreign Application Priority Data
Dec. 26, 2014 (JP) .................................. 2014-266684

(51) Int. Cl.
| C07C 45/28 | (2006.01) |
| C07C 45/57 | (2006.01) |
| C07C 49/385 | (2006.01) |
| C07C 49/587 | (2006.01) |
| C07B 61/00 | (2006.01) |
| B01J 31/02 | (2006.01) |
| C01G 41/02 | (2006.01) |
| C01B 15/01 | (2006.01) |

(52) U.S. Cl.
CPC ............ *C07C 45/28* (2013.01); *B01J 31/0239* (2013.01); *C01B 15/01* (2013.01); *C01G 41/02* (2013.01); *C07B 61/00* (2013.01); *C07C 45/57* (2013.01); *C07C 49/385* (2013.01); *C07C 49/587* (2013.01)

(58) Field of Classification Search
CPC ................................ C07C 45/28; C07C 45/57
See application file for complete search history.

(56) References Cited

U.S. PATENT DOCUMENTS

| 3,506,716 | A | 4/1970 | Peterli et al. |
| 3,778,483 | A | 12/1973 | Becker et al. |
| 2002/0025906 | A1 | 2/2002 | Hagiya et al. |
| 2004/0152592 | A1 | 8/2004 | Hagiya et al. |
| 2005/0215817 | A1 | 9/2005 | Sato et al. |
| 2010/0210673 | A1 | 8/2010 | Kon et al. |

FOREIGN PATENT DOCUMENTS

| CN | 102786398 A | 11/2012 |
| JP | 45-19903 B1 | 7/1970 |
| JP | 51-24498 B1 | 7/1976 |
| JP | 2000-159693 A | 6/2000 |
| JP | 2002-201147 A | 7/2002 |
| JP | 2002-201154 A | 7/2002 |
| JP | 2003-267905 A | 9/2003 |
| JP | 2004-59450 A | 2/2004 |
| JP | 2004-59451 A | 2/2004 |
| JP | 2007-119501 A | 5/2007 |
| JP | 2010-189317 A | 9/2010 |

OTHER PUBLICATIONS

International Search Report dated Mar. 1, 2016 in PCT/JP2015/085772 filed Dec. 22, 2015.
(Continued)

*Primary Examiner* — Sikarl A Witherspoon
(74) *Attorney, Agent, or Firm* — Oblon, McClelland, Maier & Neustadt, L.L.P.

(57) ABSTRACT

Provided is a method for producing a compound represented by general formula (I) by oxidative cleavage of a compound of formula (II), which is a bicyclic tetrasubstituted olefin compound, using hydrogen peroxide. The method for producing a compound represented by general formula (I) includes a step of subjecting a compound represented by general formula (II) to oxidative cleavage using hydrogen peroxide in the presence of an acid catalyst or in the presence of a tungstic acid compound to obtain the compound represented by general formula (I):

[Chemical Formula 1]

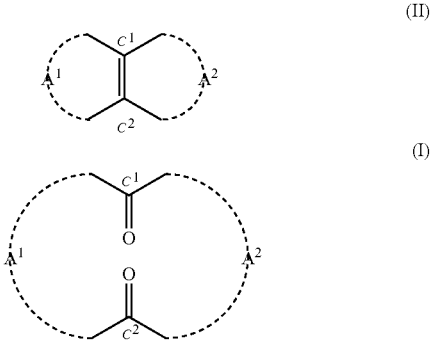

[In the formulae, formula -$A^1$- (where the front bond denotes a bond that bonds with a carbon atom $C^1$ while the back bond denotes a bond that bonds with a carbon atom $C^2$) is an alkylene group having 2 to 6 carbon atoms that may have been substituted and that may further include an ether bond, an ester bond, a secondary amino group, a thioether group, or these, and formula -$A^2$- (where the front bond denotes a bond that bonds with a carbon atom $C^1$ while the back bond denotes a bond that bonds with a carbon atom $C^2$) is an alkylene group having 4 to 10 carbon atoms that may have been substituted and that may further include an ether bond, an ester bond, a secondary amino group, a thioether group, or these.]

19 Claims, No Drawings

(56) References Cited

OTHER PUBLICATIONS

Vladimir A. D'Yakonov et al., "Synthesis of gigantic macrocyclic polyketones through catalytic cyclometalation of cycloalkynes", Tetrahedron, 2010, vol. 66, pp. 6885-6888.
Carley L. Chandler et al., "Catalytic, Asymmetric Transannular Aldolizations: Total Synthesis of (+)-Hirsutene", Journal of the American Chemical Society, 2008, vol. 130, pp. 6737-6739.
Takahito Oguchi et al., "Oxidative Cleavage of Olefins into Carboxylic Acids with Hydrogen Peroxide by Tungstic Acid", Chemistry Letters, 1989, pp. 857-860.
H.R. Sonawane et al., "On the Construction of Bicyclo [m.3.0] Bridged Alkenes: Thermal Rearrangement of Spirocyclic Vinylcyclopropanes", Tetrahedron Letters, 1992, vol. 33, No. 12, pp. 1645-1646.
Karl Griesbaum et al., "syn- and anti-Isomers of a O-Methyloxime-Substituted Tricyclic Ozonide", European Journal of Organic Chemistry, 2006, pp. 1978-1980.
Kazunori Miyamoto et al., "Iodomesitylene-Catalyzed Oxidative Cleavage of Carbon-Carbon Double and Triple Bonds Using m-Chloroperbenzoic Acid as a Terminal Oxidant", Journal of the American Chemical Society, 2009, vol. 131, pp. 1382-1383.
Extended European Search Report dated Feb. 6, 2018 in Patent Application No. 15873042.4, 5 pages.

US 10,087,129 B2

METHOD FOR PRODUCING CYCLIC DIKETONE COMPOUND

CROSS REFERENCE TO RELATED APPLICATION

This application is a National Stage entry under 35 USC 371 of PCT/JP2015/085772, filed on Dec. 22, 2015, and claims priority to Japanese Patent Application No. 2014-266684, filed on Dec. 26, 2014.

TECHNICAL FIELD

The present disclosure relates to a method for producing a compound represented by general formula (I).

BACKGROUND ART

Development of a carbon-carbon bond cleavage reaction is one of the important themes in synthetic organic chemistry. Particularly, the oxidative cleavage reaction of an olefin compound has been frequently used extensively. Conventionally, methods used frequently include a method in which sodium periodate is used as an oxidizing agent in the presence of a catalyst such as an osmium metal compound or a ruthenium metal compound, and a method in which ozone is used as an oxidizing agent (Non-Patent Documents 1 and 2). However, these methods have problems that, for example, the osmium metal compound is highly toxic, the ruthenium metal compound and the sodium periodate are expensive and produce a large amount of by-products during the reaction, the method in which ozone is used can potentially cause explosions, and furthermore, a large amount of power consumption is required for generating ozone. Thus, these methods cannot be said to be industrially suitable from the viewpoints of safety, cost, and environment.

Recently, therefore, a method for subjecting an olefin compound to oxidative cleavage in the presence of hydrogen peroxide has been attracting attention.

Patent Document 1 discloses a method for producing carboxylic acid, the method including reacting unsaturated triacylglycerol with hydrogen peroxide in the presence of a quaternary ammonium polybasic acid hydrogen salt and at least one selected from tungstic acid, heterotungstic acid, and their salts.

Furthermore, Patent Document 2 and Patent Document 3 each disclose a method for producing carboxylic acid, the methods of Patent Document 2 and Patent Document 3 being characterized by reacting an alicyclic alcohol oily solution with hydrogen peroxide and an alicyclic ketone oily solution with hydrogen peroxide, respectively, in a heterogeneous solution system in the presence of a catalyst containing a compound of a metal of Group 6 in the periodic table.

Hydrogen peroxide is safe and inexpensive. Furthermore, since it produces only water as a by-product after it is reacted, it is environmentally friendly. Thus, a method for subjecting olefin to oxidative cleavage using the hydrogen peroxide can be said to be an industrially advantageous method. However, there are only several examples that have been reported, in which hydrogen peroxide was used to subject a tetrasubstituted olefin compound to oxidative cleavage.

For example, Patent Documents 5 and 6 each disclose a method for producing ß-hydroxyhydroperoxides and ketones, the method being characterized by reacting tetrasubstituted olefin and hydrogen peroxide in the presence of a particular catalyst. The catalyst is at least one type of metal compound selected from the group consisting of tungsten metal, molybdenum metal, a tungsten compound composed of tungsten and a group IIIb element, a group IVb element, a group Vb element, or a group VIb element except oxygen, and a molybdenum compound composed of molybdenum and a group IIIb element, a group IVb element, a group Vb element, or a group VIb element except oxygen. Both Patent Documents describe that some reaction products cleave into diketones.

PRIOR ART DOCUMENTS

Patent Documents

[Patent Document 1] JP2010-189317A
[Patent Document 2] JP2004-59451A
[Patent Document 3] JP2004-59450A
[Patent Document 4] JP51(1976)-24498A
[Patent Document 5] JP2002-201154A
[Patent Document 6] JP2002-201147A

Non-Patent Documents

[Non-Patent Document 1] Tetrahedron, 66(34), 6885-6888, 2010
[Non-Patent Document 2] Journal of the American Chemical Society, 130(21), 6737-6739, 2008
[Non-Patent Document 3] Chem. Lett., 857, 1989
[Non-Patent Document 4] Tetrahedron Letters, 33, 1645, 1992
[Non-Patent Document 5] Eur. J. Org. Chem. 1978, 2006

SUMMARY OF THE INVENTION

Problem to be Solved by the Invention

Oxidative cleavage of a tetrasubstituted olefin compound is industrially very important as a method for constructing a medium to large membered ring skeleton that is often seen in, for example, a specific bioactive compound, a perfume compound, and intermediates thereof (Patent Document 4, Non-Patent Documents 4 and 5). Therefore, it is desired to develop an oxidative cleavage reaction of tetrasubstituted olefin that is highly versatile, safe, and harmless to the environment.

It is an object of the present disclosure to provide a method for producing a compound represented by general formula (I) by oxidative cleavage of a compound of formula (II), which is a bicyclic tetrasubstituted olefin compound, using hydrogen peroxide.

Means for Solving the Problem

In order to achieve the above object, the present inventors conducted intensive studies of the oxidative cleavage of a tetrasubstituted olefin compound using hydrogen peroxide in the presence of an acid catalyst or in the presence of a tungstic acid compound. As a result, they found that surprisingly, an oxidative cleavage reaction specifically proceeds in a bicyclic tetrasubstituted olefin compound. Furthermore, under the same conditions, the reaction did not proceed in a linear or monocyclic tetrasubstituted olefin compound.

That is, the present disclosure is a method for producing a compound represented by general formula (I), the method including a step of subjecting a compound represented by general formula (II) to oxidative cleavage using hydrogen peroxide in the presence of an acid catalyst or in the presence of a tungstic acid compound to obtain the compound represented by general formula (I).

[Chemical Formula 1]

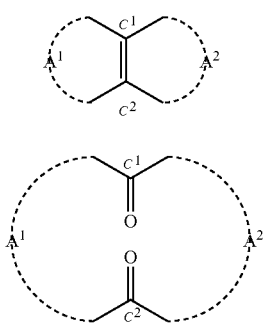

In the above formulae,
formula -A¹- (where the front bond denotes a bond that bonds with a carbon atom $C^1$ while the back bond denotes a bond that bonds with a carbon atom $C^2$) is an alkylene group having 2 to 6 carbon atoms that may have been substituted and that may further include an ether bond, an ester bond, a secondary amino group, a thioether group, or these, and
formula -A²- (where the front bond denotes a bond that bonds with a carbon atom $C^1$ while the back bond denotes a bond that bonds with a carbon atom $C^2$) is an alkylene group having 4 to 10 carbon atoms that may have been substituted and that may further include an ether bond, an ester bond, a secondary amino group, a thioether group, or these.

Effects of the Invention

According to the present disclosure, a compound represented by general formula (I) can be produced by oxidative cleavage of a bicyclic tetrasubstituted olefin compound using hydrogen peroxide in the presence of an acid catalyst or in the presence of a tungstic acid compound.

DESCRIPTION OF PREFERRED EMBODIMENTS

The present disclosure relates to a method for producing a compound represented by general formula (I), the method including a step of subjecting a compound represented by general formula (II) (hereinafter may be referred to as a "compound of formula (II)") to oxidative cleavage using hydrogen peroxide in the presence of an acid catalyst or in the presence of a tungstic acid compound to obtain the compound represented by general formula (I) (hereinafter may be referred to as a "compound of formula (I)").

[Chemical Formula 2]

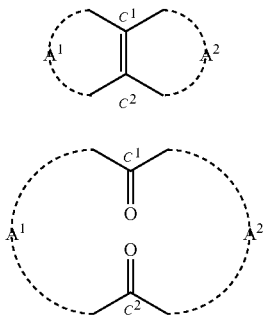

In the above formulae,
formula -A¹- (where the front bond denotes a bond that bonds with a carbon atom $C^1$ while the back bond denotes a bond that bonds with a carbon atom $C^2$) is an alkylene group having 2 to 6 carbon atoms that may have been substituted and that may further include an ether bond, an ester bond, a secondary amino group, a thioether group, or these, and
formula -A²- (where the front bond denotes a bond that bonds with a carbon atom $C^1$ while the back bond denotes a bond that bonds with a carbon atom $C^2$) is an alkylene group having 4 to 10 carbon atoms that may have been substituted and that may further include an ether bond, an ester bond, a secondary amino group, a thioether group, or these.

It is not clear why a compound represented by general formula (I) can be produced by oxidative cleavage of a bicyclic tetrasubstituted olefin compound using hydrogen peroxide in the presence of an acid catalyst or in the presence of a tungstic acid compound. However, since the reaction did not proceed in an acyclic or monocyclic tetrasubstituted olefin compound, it can be considered that the two ring structures restrict the flexibility of the four bonds formed as double bonds, which made oxidative cleavage possible even using a relatively mild oxidizing agent such as hydrogen peroxide.

In the above formula (II) and formula (I), "an alkylene group having 2 to 6 carbon atoms" in the phrase "an alkylene group having 2 to 6 carbon atoms that may have been substituted and that may further include an ether bond, an ester bond, a secondary amino group, a thioether group, or these" in the formula -A¹- is represented by, for example, formula —$(CH_2)_2$—, formula —$(CH_2)_3$—, formula —$(CH_2)_4$—, formula —$(CH_2)_5$—, or formula —$(CH_2)_6$—, and it is preferably formula —$(CH_2)_3$— or formula —$(CH_2)_4$—. Furthermore, the above-mentioned alkylene group having 2 to 6 carbon atoms that may have been substituted is preferably an alkylene group having 3 or 4 carbon atoms that may have been substituted.

In the above formula (II) and formula (I), "an alkylene group having 2 to 6 carbon atoms that may further include an ether bond, an ester bond, a secondary amino group, a thioether group, or these" in the phrase "an alkylene group having 2 to 6 carbon atoms that may have been substituted and that may further include an ether bond, an ester bond, a secondary amino group, a thioether group, or these" in the formula -A¹- is an alkylene group having 2 to 6 carbon atoms that includes, in combination, at least one selected from the group consisting of for example, an ether bond (—O—), an ester bond (—C(=O)—O— or —O—C(=O)—), a secondary amino group (—NH—), and a thioether group (—S—). However, the carbon atom of the ester bond is not included in the 2 to 6 carbon atoms. Examples of the "alkylene group having 2 to 6 carbon atoms that may further include an ether bond, an ester bond, a secondary amino group, a thioether group, or these" include formula —$CH_2$—O—$CH_2$—, formula —$CH_2$—C(=O)—O—$CH_2$—, formula —$CH_2$—NH—$CH_2$—, formula —$CH_2$—S—$CH_2$—, formula —$(CH_2)_2$—O—$CH_2$—, formula —$(CH_2)_2$—NH—$(CH_2)_2$—, formula —$(CH_2)_2$—, formula —$(CH_2)_3$—, formula —$(CH_2)_4$—, formula —$(CH_2)_5$—, and formula —$(CH_2)_6$—, and it is preferably formula —$(CH_2)_3$— or formula —$(CH_2)_4$—.

In the above formula (II) and formula (I), "an alkylene group having 4 to 10 carbon atoms" in the phrase "an alkylene group having 4 to 10 carbon atoms that may have been substituted and that may further include an ether bond, an ester bond, a secondary amino group, a thioether group, or these" in the formula -$A^2$- is represented by, for example, formula —$(CH_2)_4$—, formula —$(CH_2)_5$—, formula —$(CH_2)_6$—, formula —$(CH_2)_7$—, formula —$(CH_2)_8$—, formula —$(CH_2)_9$—, or formula —$(CH_2)_{10}$—, and it is preferably formula —$(CH_2)_4$—, formula —$(CH_2)_6$—, formula —$(CH_2)_8$—, or formula —$(CH_2)_{10}$—, more preferably formula —$(CH_2)_4$—, formula —$(CH_2)_6$—, or formula —$(CH_2)_{10}$—. Furthermore, the above-mentioned alkylene group having 4 to 10 carbon atoms that may have been substituted is preferably an alkylene group having 4, 6, 8, or 10 carbon atoms, more preferably an alkylene group having 4, 6, or 10 carbon atoms, each of which may have been substituted.

In the above formula (II) and formula (I), "an alkylene group having 4 to 10 carbon atoms that may further include an ether bond, an ester bond, a secondary amino group, a thioether group, or these" in the phrase "an alkylene group having 4 to 10 carbon atoms that may have been substituted and that may further include an ether bond, an ester bond, a secondary amino group, a thioether group, or these" in the formula -$A^2$- is an alkylene group having 4 to 10 carbon atoms that includes, in combination, at least one selected from the group consisting of, for example, an ether bond (—O—), an ester bond (—C(=O)—O— or —O—C(=O)—), a secondary amino group (—NH—), and a thioether group (—S—). However, the carbon atom of the ester bond is not included in the 4 to 10 carbon atoms. Examples of the "alkylene group having 4 to 10 carbon atoms that may further include an ether bond, an ester bond, a secondary amino group, a thioether group, or these" include formula —$(CH_2)_2$—O—$(CH_2)_2$—, formula —$(CH_2)_2$—NH—$(CH_2)_2$—, formula —$(CH_2)_4$—, formula —$(CH_2)_5$—, formula —$(CH_2)_6$—, formula —$(CH_2)_7$—, formula —$(CH_2)_8$—, formula —$(CH_2)_9$—, and formula —$(CH_2)_{10}$—, and it is preferably formula —$(CH_2)_2$—O—$(CH_2)_2$—, formula —$(CH_2)_4$—, formula —$(CH_2)_6$—, formula —$(CH_2)_8$—, or formula —$(CH_2)_{10}$—, more preferably formula —$(CH_2)_4$—, formula —$(CH_2)_6$—, or formula —$(CH_2)_{10}$—.

The "alkylene group having 2 to 6 carbon atoms that may have been substituted and that may further include an ether bond, an ester bond, a secondary amino group, a thioether group, or these" in the formula -$A^1$- and the "alkylene group having 4 to 10 carbon atoms that may have been substituted and that may further include an ether bond, an ester bond, a secondary amino group, a thioether group, or these" in the formula -$A^2$- are "an alkylene group having 2 to 6 carbon atoms that may further include an ether bond, an ester bond, a secondary amino group, a thioether group, or these" and "an alkylene group having 4 to 10 carbon atoms that may further include an ether bond, an ester bond, a secondary amino group, a thioether group, or these", respectively, each of which may have at least one substitute, preferably one or two substitutes. Examples of the substituent include an alkyl group, an alkoxy group, an alkylamino group, an alkoxycarbonyl group, an alkanoyl group, an aryl group, an aralkyl group, an aryloxy group, an acyloxy group, a carboxy group, a halogen atom, a carbon ring, and a heterocyclic ring, and it is preferably an alkyl group, an alkoxycarbonyl group, or an alkoxy group, more preferably an alkyl group.

The alkyl group is, for example, an alkyl group having 1 to 6 carbon atoms, preferably an alkyl group having 1 to 4 carbon atoms, and more preferably an alkyl group having 1 or 2 carbon atoms.

The alkoxy group is, for example, an alkoxy group having 1 to 6 carbon atoms, preferably an alkoxy group having 1 to 4 carbon atoms, and more preferably an alkoxy group having 1 or 2 carbon atoms.

The alkylamino group is, for example, an alkylamino group having 1 to 6 carbon atoms, preferably an alkylamino group having 1 to 4 carbon atoms, and more preferably an alkylamino group having 1 or 2 carbon atoms. The alkylamino group may be a monoalkylamino group or a dialkylamino group.

The alkoxycarbonyl group is, for example, an alkoxycarbonyl group having 1 to 6 carbon atoms in the alkyl moiety, preferably an alkoxycarbonyl group having 1 to 4 carbon atoms in the alkyl moiety, and more preferably an alkoxycarbonyl group having 1 or 2 carbon atoms in the alkyl moiety.

The alkanoyl group is, for example, an alkanoyl group having 1 to 6 carbon atoms in the alkyl moiety, preferably an alkanoyl group having 1 to 4 carbon atoms in the alkyl moiety, and more preferably an alkanoyl group having 1 or 2 carbon atoms in the alkyl moiety.

The aryl group is, for example, an aryl group having 6 to 10 carbon atoms.

The aralkyl group, which denotes an arylalkyl group, is, for example, an aralkyl group having 6 to 10 carbon atoms in the aryl moiety and 1 to 6 carbon atoms in the alkyl moiety, preferably an aralkyl group having 6 to 10 carbon atoms in the aryl moiety and 1 to 4 carbon atoms in the alkyl moiety, and more preferably an aralkyl group having 6 to 10 carbon atoms in the aryl moiety and 1 or 2 carbon atoms in the alkyl moiety.

The aryloxy group is, for example, an aryloxy group having 6 to 10 carbon atoms.

The acyloxy group is, for example, an alkylcarbonyloxy group having 1 to 6 carbon atoms in the alkyl moiety, preferably an alkylcarbonyloxy group having 1 to 4 carbon atoms in the alkyl moiety, and more preferably an alkylcarbonyloxy group having 1 or 2 carbon atoms in the alkyl moiety.

Examples of the halogen atom include fluorine, chlorine, bromine, and iodine.

The carbon ring denotes saturated or unsaturated cyclic hydrocarbon and examples thereof include saturated cyclic hydrocarbon having 3 to 10 carbon atoms and unsaturated cyclic hydrocarbon having 4 to 10 carbon atoms.

The heterocyclic ring denotes saturated or unsaturated cyclic hydrocarbon including a heteroatom (for example, oxygen, nitrogen, or sulfur). Examples thereof include saturated cyclic hydrocarbon having 3 to 10 carbon atoms including a heteroatom and unsaturated cyclic hydrocarbon having 4 to 10 carbon atoms including a heteroatom.

Two or more of the substituents may be bonded to each other to form a carbon ring or a heterocyclic ring.

Examples of the "alkylene group having 2 to 6 carbon atoms that may have been substituted and that may further include an ether bond, an ester bond, a secondary amino group, a thioether group, or these" in the formula -$A^1$- include formula —$CH_2$—O—$CH_2$—, formula —$CH_2$—C(=O)—O—$CH_2$—, formula —$CH_2$—NH—$CH_2$—, formula —$CH_2$—S—$CH_2$—, formula —$(CH_2)_2$—O—$CH_2$—, formula —$(CH_2)_2$—NH—$(CH_2)_2$—, formula —$(CH_2)_2$—, formula —$(CH_2)_3$—, formula —$(CH_2)_4$—, formula —$(CH_2)_5$—, and formula —$(CH_2)_6$—, each of which may have been substituted. It is preferably formula —$(CH_2)_3$— or formula —$(CH_2)_4$—, more preferably formula —$(CH_2)_3$—, formula —$(CH_2)_4$—, or formula —$CH_2$—CH($CH_3$)—$CH_2$—, each of which may have been substituted.

Examples of the "alkylene group having 4 to 10 carbon atoms that may have been substituted and that may further include an ether bond, an ester bond, a secondary amino group, a thioether group, or these" in the formula -A²- include formula —(CH₂)₂—O—(CH₂)₂—, formula —(CH₂)₂—NH—(CH₂)₂—, formula —(CH₂)₄—, formula —(CH₂)₅—, formula —(CH₂)₆—, formula —(CH₂)₇—, formula —(CH₂)₈—, formula —(CH₂)₉—, and formula —(CH₂)₁₀—, each of which may have been substituted. It is preferably formula —(CH₂)₂—O—(CH₂)₂—, formula —(CH₂)₄—, formula —(CH₂)₆—, formula —(CH₂)₈—, or formula —(CH₂)₁₀—, more preferably formula —(CH₂)₂—O—(CH₂)₂—, formula —(CH₂)₄—, formula —(CH₂)₆—, formula —(CH₂)₈—, or formula —(CH₂)₁₀—, and further preferably formula —(CH₂)₄—, formula —(CH₂)₆—, or formula —(CH₂)₁₀—, each of which may have been substituted.

From the viewpoint of using a resultant compound of general formula (I) as a precursor of a perfume compound, the formula -A¹- (where the front bond denotes a bond that bonds with a carbon atom C¹ while the back bond denotes a bond that bonds with a carbon atom C²) is preferably an alkylene group having 3 or 4 carbon atoms, more preferably formula —(CH₂)₃—, formula —CH₂—CH(CH₃)—CH₂, or formula —(CH₂)₄—, and further preferably formula —CH₂—CH(CH₃)—CH₂—, each of which may have been substituted.

From the viewpoint of using a resultant compound of general formula (I) as a precursor of a perfume compound, the formula -A²- (where the front bond denotes a bond that bonds with a carbon atom C¹ while the back bond denotes a bond that bonds with a carbon atom C²) is preferably an alkylene group having 4, 6, 8, or 10 carbon atoms, more preferably formula —(CH₂)₄—, formula —CH₂—CH(CH₃)—CH₂—CH₂—, formula —CH₂—CH₂—CH(CH₃)—CH₂—, formula —(CH₂)₆—, formula —(CH₂)₈—, or formula —(CH₂)₁₀—, further preferably formula —(CH₂)₄—, formula —(CH₂)₆—, formula —(CH₂)₈—, or formula —(CH₂)₁₀—, still further preferably formula —(CH₂)₄—, formula —(CH₂)₆—, or formula —(CH₂)₁₀—, and yet further preferably formula —(CH₂)₁₀—, each of which may have been substituted.

The compound represented by general formula (II) is represented by, for example, the following formulae. From the viewpoint of using a resultant compound of general formula (I) as a precursor of a perfume compound, it is preferably a compound represented by formula (i), a compound represented by formula (iii), a compound represented by formula (vii), or a compound represented by formula (viii), more preferably a compound represented by formula (vii). The compound represented by formula (vii) is 14-methylbicyclo[10.3.0]pentadecene[1(12)].

[Chemical Formula 3]

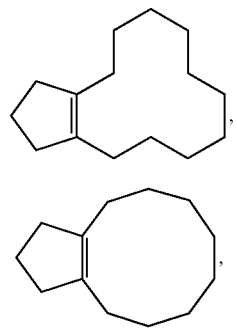

(i)

(ii)

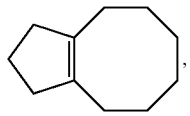

(iii)

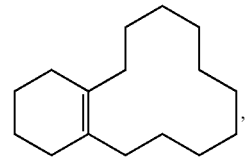

(iv)

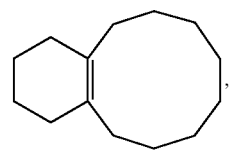

(v)

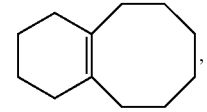

(vi)

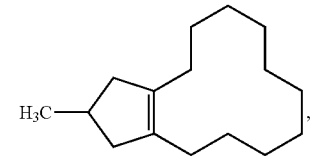

(vii)

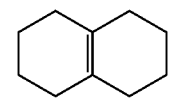

(viii)

The compound represented by general formula (I) is, for example, 3-methyl-1,5-cyclopentadecanedione represented by the following formula (1).

[Chemical Formula 4]

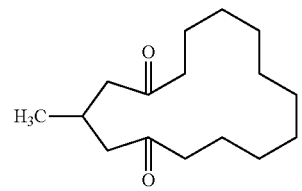

(1)

In the present disclosure, the acid catalyst to be used can be any of Bronsted acid, Lewis acid, etc.

As the Bronsted acid, a Bronsted acid having a pKa (in water) of not more than 2.0, for example, sulfuric acid (pKa=1.96), phosphoric acid (pKa=1.83), trifluoroacetic acid (pKa=−0.3), or p-toluenesulfonic acid (pKa=−2.8), can be used.

As the Lewis acid, for example, metal chloride or metal triflate can be used. Examples of the metal chloride include molybdenum chloride, tungsten chloride, aluminum chloride, and tin chloride. Examples of the metal triflate include indium triflate and scandium triflate.

In the present disclosure, the tungstic acid compound is more preferably of an acid type that substantially generates proton (H+) when it reacts with hydrogen peroxide to form metal peroxide.

Examples of the tungstic acid compound include tungstic acid, isopolytungstic acid, and heteropolytungstic acid, and it is preferably tungstic acid.

Examples of the tungstic acid include orthotungstic acid ($H_2WO_4$), metatungstic acid ($H_6[H_2W_{12}O_{40}]$), paratungstic acid ($H_6[H_{10}W_{12}O_{46}]$), and phosphotungstic acid ($H_3PW_{12}O_{40}(nH_2O)$). Particularly, orthotungetic acid ($H_2WO_4$) is preferably used. The tungstic acids may be used alone or two or more of them may be used in combination.

The hydration structure of the orthotungstic acid is not particularly limited and monohydrate ($H_2WO_4$) or dehydrate ($H_4WO_5$) can be used but monohydrate is preferably used. The orthotungstic acid may be used alone or two or more of them may be combined together.

Among the above-mentioned acid catalysts and tungstic acid compounds, a Bronsted acid having a pKa of not more than 2.0 and a tungstic acid compound are preferably used, tungstic acid is used more preferably, and orthotungatic acid is used further preferably. In the present disclosure, the acid catalyst and the tungstic acid compound may be used simultaneously or only one of them may be used.

From the viewpoint of improving the reaction yield, the amount of the acid catalyst to be used is preferably 1:0.001 to 1:0.7, more preferably 1:0.005 to 1:0.5, and further preferably 1:0.01 to 1:0.3, in terms of molar ratio of the compound of formula (II) to the acid catalyst (the compound of formula (II): the acid catalyst).

From the viewpoint of improving the reaction yield, the amount of the tungstic acid compound to be used is preferably 1:0.001 to 1:0.7, more preferably 1:0.005 to 1:0.5, and further preferably 1:0.01 to 1:0.3, in terms of molar ratio of the compound of formula (I) to the tungstic acid compound (the compound of formula (II): the tungstic acid compound).

From the viewpoints of production cost and production efficiency, the amount of the hydrogen peroxide to be used is preferably 1:10 to 1:2, more preferably 1:7 to 1:2, and further preferably 1:5 to 1:2.5, in terms of molar ratio of the compound of formula (II) to the hydrogen peroxide (the compound of formula (II): the hydrogen peroxide).

The concentration of the hydrogen peroxide to be used in the present disclosure is not particularly limited but in general, it is 1 to 80% by mass. From the viewpoints of safety and reaction yield, preferably it is selected from the range of 30 to 60% by mass.

The reaction temperature employed in the method of the present disclosure is generally 0° C. to 100° C. From the viewpoint of improving the reaction yield safely, it is preferably at least 20° C. but is preferably not higher than 80° C., more preferably not higher than 50° C.

In the method of the present disclosure, the reaction may be carried out in the presence of an organic solvent. The organic solvent is not particularly limited as long as it is a solvent that allows the reaction solution to be homogeneous. Examples of the organic solvent include ethers and alcohols. Particularly, from the view point of the reaction yield, the organic solvent to be used is preferably alcohols, more preferably saturated aliphatic alcohol and further preferably t-butyl alcohol.

The present disclosure further relates to a method for producing a compound represented by general formula (III) (hereinafter may be referred to as a "compound of formula (I)"), the method including reducing a compound represented by general formula (I) to obtain the compound represented by general formula (III).

[Chemical Formula 5]

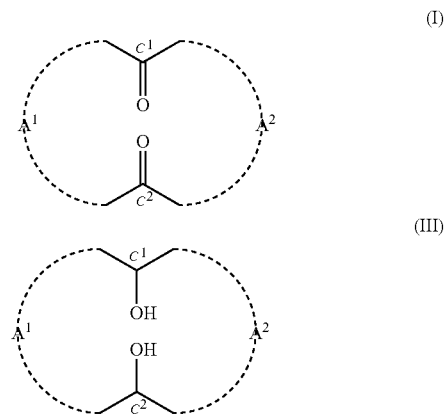

In the above formulae,
formula -$A^1$- (where the front bond denotes a bond that bonds with a carbon atom $C^1$ while the back bond denotes a bond that bonds with a carbon atom $C^2$) is an alkylene group having 2 to 6 carbon atoms that may have been substituted and that may further include an ether bond, an ester bond, a secondary amino group, a thioether group, or these, and formula -$A^2$- (where the front bond denotes a bond that bonds with a carbon atom $C^1$ while the back bond denotes a bond that bonds with a carbon atom $C^2$) is an alkylene group having 4 to 10 carbon atoms that may have been substituted and that may further include an ether bond, an ester bond, a secondary amino group, a thioether group, or these.

The definition of the formula -$A^1$-, "an alkylene group having 2 to 6 carbon atoms that may have been substituted and that may further include an ether bond, an ester bond, a secondary amino group, a thioether group, or these," and the definition of the formula -$A^2$-, "an alkylene group having 4 to 10 carbon atoms that may have been substituted and that may further include an ether bond, an ester bond, a secondary amino group, a thioether group, or these," in the formula (III) are the same as the definition of the formula -$A^1$-, "an alkylene group having 2 to 6 carbon atoms that may have been substituted and that may further include an ether bond, an ester bond, a secondary amino group, a thioether group, or these," and the definition of the formula -$A^2$-, "an alkylene group having 4 to 10 carbon atoms that may have been substituted and that may further include an ether bond, an ester bond, a secondary amino group, a thioether group, or these," in the formula (I) and formula (II), respectively.

The present disclosure further provides a method for producing a cyclic ketone compound represented by formula (3). The cyclic ketone compound represented by formula (3) is a mixture of 3-methyl-4-cyclopentadecen-1-one and 3-methyl-5-cyclopentadecen-1-one and is known as Muscenone (manufactured by Firmenich). The cyclic ketone compound represented by formula (3), which is a musk fragrance material, is a cyclic compound that is excellent in biodegradability and fragrance retention and has an elegant feel. There is a need to develop a production method that meets the recent increasing needs for synthetic musk fragrances, has high production safety, and is excellent in production efficiency. The method for producing a cyclic ketone compound represented by formula (3), which uses 3-methyl-1,5-cyclopentadecanedione (1) that is obtained by the method of the present disclosure, includes either one of the following step (a) or step (b).

[Chemical Formula 6]

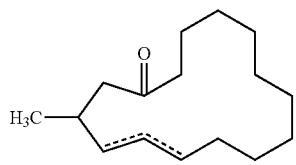
(3)

A step (a) of partially reducing the 3-methyl-1,5-cyclopentadecanedione and then dehydrating it to obtain the cyclic ketone compound represented by formula (3), or a step (b) of reducing the 3-methyl-1,5-cyclopentadecanedione, then enoletherifying it, and subsequently, decyclizing it to obtain Muscenone.

The step (a) includes: for example,
a step (a-1) of partially reducing the 3-methyl-1,5-cyclopentadecanedione (1) to obtain 3-methylcyclopentadecanol-5-one (2); and
a step (a-2) of dehydrating the 3-methylcyclopentadecanol-5-one (2) to obtain the cyclic ketone compound represented by formula (3).

[Chemical Formula 7]

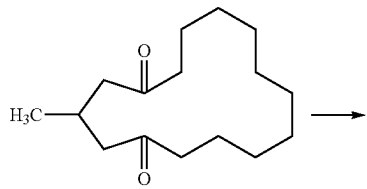

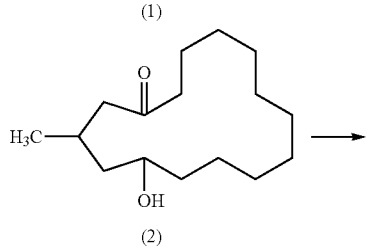

The step (b) includes: for example,
a step (b-1) of reducing the 3-methyl-1,5-cyclopentadecanedione (1) to obtain 3-methylcyclopentadecane-1,5-diol (4);
a step (b-2) of partially oxidizing and enoletherifying the 3-methylcyclopentadecane-1,5-diol (4) to obtain 16-oxa-3-methylbicyclo[10.3.1]pentadec-1-en (5); and
a step (b-3) of decyclizing the 16-oxa-3-methylbicyclo[10.3.1]pentadec-1-en (5) to obtain the cyclic ketone compound represented by formula (3).

[Chemical Formula 8]

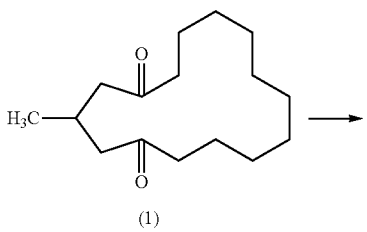

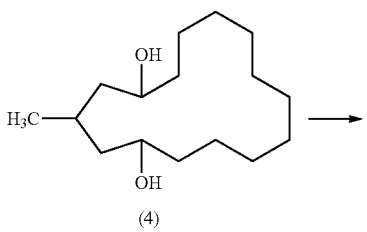

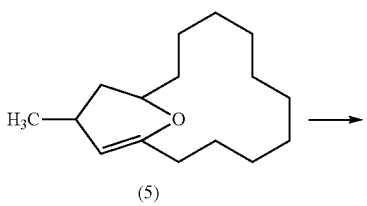

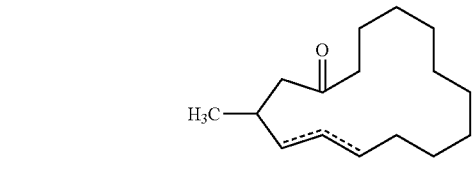

The 3-methyl-1,5-cyclopentadecanedione (1) can be obtained by a method for producing a compound represented by formula (I) of the present disclosure.

First, a method for producing a cyclic ketone compound represented by formula (3), which includes the step (a), is described.

The step (a) includes:
a step (a-1) of partially reducing the 3-methyl-1,5-cyclopentadecanedione (1) to obtain 3-methylcyclopentadecanol-5-one (2), and
a step (a-2) of dehydrating the 3-methylcyclopentadecanol-5-one (2) to obtain the cyclic ketone compound represented by formula (3).

[Chemical Formula 9]

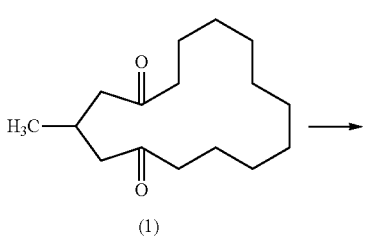

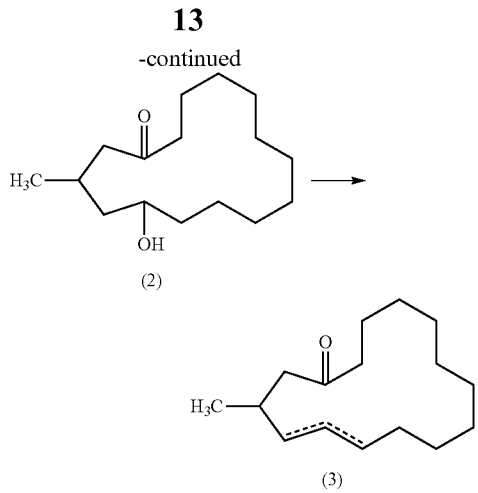

Examples of the method for partially reducing the 3-methyl-1,5-cyclopentadecanedione (1) in the step (a-1) include a method in which metal hydride, for example, sodium borohydride or sodium hydride, is used, and a method in which hydrogenation is carried out in the presence of a metal catalyst. From the viewpoints of safety and reaction yield, the method in which hydrogenation is carried out in the presence of a metal catalyst is preferred.

The metal catalyst to be used in the method in which hydrogenation is carried out can be, for example, palladium carbon or Raney nickel. From the viewpoint that hydrogenation can be carried out under mild reaction conditions, the metal catalyst to be used in the method in which hydrogenation is carried out is preferably Raney nickel.

In the step (a-1), from the viewpoints of reaction yield and cost, the amount of the metal catalyst to be used with respect to the 3-methyl-1,5-cyclopentadecanedione (1) is preferably 1:0.01 to 1:1, more preferably 1:0.1 to 1:0.5, in terms of molar ratio of the 3-methyl-1,5-cyclopentadecanedione (1) to the metal catalyst [the 3-methyl-1,5-cyclopentadecanedione (1): the metal catalyst].

The reaction temperature in the step (a-1) is preferably at least 0° C. from the viewpoint of improving the reaction yield but is preferably not higher than 100° C., more preferably not higher than 50° C., and further preferably not higher than 30° C. from the viewpoint of preventing side reactions.

From the viewpoint of improving the reaction yield, the reaction time in the step (a-1) is preferably at least 0.1 hour, more preferably at least 0.5 hour, but is preferably not more than ten hours, more preferably not more than three hours, and further preferably not more than one hour.

From the viewpoints of safety and reaction selectivity, the hydrogen pressure for the hydrogenation is preferably at least 0.1 MPa but is preferably not higher than 2.0 MPa, more preferably not higher than 1.0 MPa.

In the step (a-1), the reaction may be carried out in the presence of an organic solvent. The organic solvent is not particularly limited as long as it is a solvent that dissolves a reactant. Examples of the organic solvent include alcohols. Particularly, from the viewpoints of production efficiency and cost, a lower alcohol having 1 to 3 carbon atoms is more preferably used.

Examples of the method for dehydrating the 3-methylcyclopentadecanol-5-one (2) in the step (a-2) include a method for dehydrating it in the presence of acid.

Examples of the acid to be used in the step (a-2) include sulfuric acid, phosphoric acid, and benzenesulfonic acid. From the viewpoints of equipment load and reaction yield, benzenesulfonic acid is preferred.

In the step (a-2), from the viewpoints of production cost and reaction yield, the amount of the acid to be used with respect to the 3-methylcyclopentadecanol-5-one (2) is preferably 1:0.01 to 1:1, more preferably 1:0.05 to 1:0.3, in terms of molar ratio of the 3-methylcyclopentadecanol-5-one (2) to the acid (the 3-methylcyclopentadecanol-5-one (2): the acid).

The reaction temperature in the step (a-2) is preferably at least 20° C., more preferably at least 50° C., and further preferably at least 70° C. from the viewpoint of improving the reaction yield, but is preferably not higher than 200° C., more preferably not higher than 150° C., and further preferably not higher than 130° C. from the viewpoint of safety.

From the viewpoint of improving the reaction yield, the reaction time in the step (a-2) is preferably at least 0.25 hour, more preferably at least 0.5 hour, but is preferably not more than 20 hours, more preferably not more than ten hours, and further preferably not more than three hours.

In the step (a-2), the reaction may be carried out in the presence of an organic solvent. The organic solvent is not particularly limited as long as it is a solvent that forms an azeotrope with water. Examples of the organic solvent include hydrocarbons, but from the viewpoint of dehydration efficiency, toluene is more preferably used.

Furthermore, a method for producing a cyclic ketone compound represented by formula (3), which includes the step (b), is described.

The step (b) includes:
a step (b-1) of reducing the 3-methyl-1,5-cyclopentadecanedione (1) to obtain 3-methylcyclopentadecane-1,5-diol (4);
a step (b-2) of partially oxidizing and enoletherifying the 3-methylcyclopentadecane-1,5-diol (4) to obtain 16-oxa-3-methylbicyclo[10.3.1]pentadec-1-en (5); and
a step (b-3) of decyclizing the 16-oxa-3-methylbicyclo[10.3.1]pentadec-1-en (5) to obtain the cyclic ketone compound represented by formula (3).

[Chemical Formula 10]

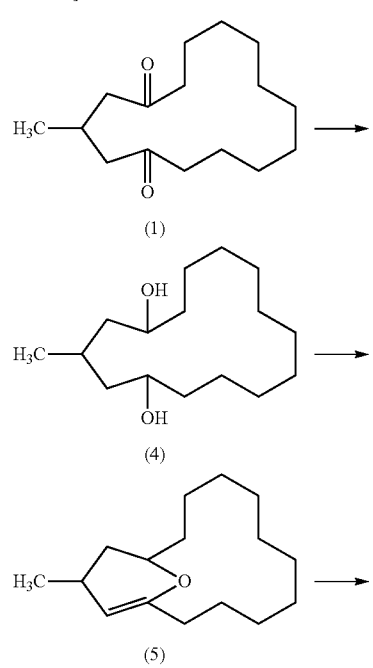

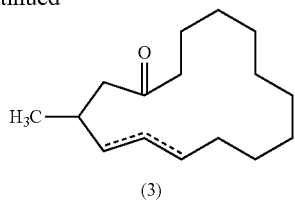

(3)

Examples of the method for partially reducing the 3-methyl-1,5-cyclopentadecanedione (1) in the step (b-1) include a method in which metal hydride, for example, sodium borohydride or sodium hydride, is used, and a method in which hydrogenation is carried out in the presence of a metal catalyst. From the viewpoints of safety and reaction yield, the method in which hydrogenation is carried out in the presence of a metal catalyst is preferred.

The metal catalyst to be used in the method in which hydrogenation is carried out can be, for example, palladium carbon or Raney nickel. From the viewpoint that hydrogenation can be carried out under mild reaction conditions, Raney nickel is preferably used.

In the step (b-1), from the viewpoints of reaction yield and cost, the amount of the metal catalyst to be used with respect to the 3-methyl-1,5-cyclopentadecanedione (1) is preferably 1:0.01 to 1:1, more preferably 1:0.1 to 1:0.5, in terms of molar ratio of the 3-methyl-1,5-cyclopentadecanedione (1) to the metal catalyst (the 3-methyl-1,5-cyclopentadecanedione (1): the metal catalyst).

The reaction temperature in the step (b-1) is preferably at least 0° C. from the viewpoint of improving the reaction yield but is preferably not higher than 100° C., more preferably not higher than 50° C., and further preferably not higher than 30° C. from the viewpoint of preventing side reactions.

From the viewpoint of improving the reaction yield, the reaction time in the step (b-1) is preferably at least one hour, more preferably at least five hours, and further preferably at least ten hours, but is preferably not more than 30 hours, more preferably not more than 25 hours.

From the viewpoints of safety and reaction selectivity, the hydrogen pressure for the hydrogenation is preferably at least 0.1 MPa but is preferably not higher than 2.0 MPa, more preferably not higher than 1.0 MPa.

In the step (b-1), the reaction may be carried out in the presence of an organic solvent. The organic solvent is not particularly limited as long as it is a solvent that dissolves a reactant. Examples of the organic solvent include alcohols. Particularly, from the viewpoints of production efficiency and cost, a lower alcohol having 1 to 3 carbon atoms is more preferably used.

Examples of the method for partially oxidizing and enoletherifying the 3-methylcyclopentadecane-1,5-diol (4) in the step (b-2) include a method for partially oxidizing and enoletherifying it in the presence of a metal catalyst.

The metal catalyst to be used in the step (b-2) can be a metal catalyst having oxidizability, for example, aluminum oxide, iron oxide, or Raney copper. However, from the viewpoint of improving the reaction yield, Raney copper is preferably used.

In the step (b-2), the amount of the metal catalyst to be used with respect to the 3-methylcyclopentadecane-1,5-diol (4) is preferably 1:0.01 to 1:1 from the viewpoints of reaction yield and cost and is more preferably 1:0.05 to 1:0.3 from the viewpoints of reducing the reaction time and waste, in terms of molar ratio of the 3-methylcyclopentadecane-1,5-diol (4) to the metal catalyst (the 3-methylcyclopentadecane-1,5-diol (4): the metal catalyst).

The reaction temperature in the step (b-2) is preferably at least 100° C., more preferably at least 120° C. from the viewpoint of improving the reaction yield, but is preferably not higher than 300° C., more preferably not higher than 200° C., and further preferably not higher than 180° C. from the viewpoint of preventing side reactions.

The reaction time in the step (b-2) is preferably at least one hour, more preferably at least two hours from the viewpoint of improving the reaction yield, but is preferably not more than 20 hours, more preferably not more than ten hours, and further preferably not more than five hours from the viewpoint of improving productivity.

Examples of the method for decyclizing the 16-oxa-3-methylbicyclo[10.3.1]pentadec-1-en (5) in the step (b-3) include a method for decyclizing it in the presence of acid.

Examples of the acid to be used in the step (b-3) include sulfuric acid, phosphoric acid, and benzenesulfonic acid. From the viewpoints of handleability and reaction yield, phosphoric acid is preferred.

In the step (b-3), from the viewpoints of production efficiency and reaction yield, the amount of the acid to be used with respect to the 16-oxa-3-methylbicyclo[10.3.1]pentadec-1-en (5) is preferably 1:0.01 to 1:1, more preferably 1:0.1 to 1:0.5, in terms of molar ratio of the 16-oxa-3-methylbicyclo[10.3.1]pentadec-1-en (5) to the acid (the 16-oxa-3-methylbicyclo[10.3.1]pentadec-1-en (5): the acid).

The reaction temperature in the step (b-3) is preferably at least 20° C., more preferably at least 50° C., and further preferably at least 70° C. from the viewpoint of improving the reaction yield, but is preferably not higher than 200° C., more preferably not higher than 150° C., and further preferably not higher than 130° C. from the viewpoint of preventing side reactions.

From the viewpoint of improving the reaction yield, the reaction time in the step (b-3) is preferably at least 0.5 hour, more preferably at least one hour, but is preferably not more than 20 hours, more preferably not more than ten hours, and further preferably not more than five hours.

In the step (b-3), the reaction may be carried out in the presence of an organic solvent. The organic solvent is not particularly limited as long as it is a solvent that forms an azeotrope with water. Examples of the organic solvent include hydrocarbons, but from the viewpoint of dehydration efficiency, toluene is more preferably used.

With respect to the embodiments described above, the present disclosure further discloses a method for producing a compound represented by general formula (I) and a method for producing a cyclic ketone compound represented by formula (3).

<1> A method for producing a compound represented by general formula (I), the method including a step of subjecting a compound represented by general formula (II) to oxidative cleavage using hydrogen peroxide in the presence of an acid catalyst or in the presence of a tungstic acid compound to obtain the compound represented by general formula (I).

[Chemical Formula 11]

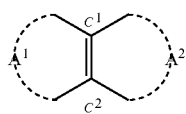

(II)

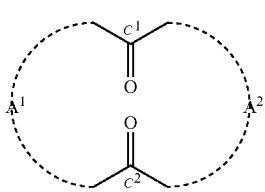

In the above formulae, formula -A$^1$- (where the front bond denotes a bond that bonds with a carbon atom C$^1$ while the back bond denotes a bond that bonds with a carbon atom C$_2$) is an alkylene group having 2 to 6 carbon atoms that may have been substituted and that may further include an ether bond, an ester bond, a secondary amino group, a thioether group, or these, and formula -A$^2$- (where the front bond denotes a bond that bonds with a carbon atom C$^1$ while the back bond denotes a bond that bonds with a carbon atom C$_2$) is an alkylene group having 4 to 10 carbon atoms that may have been substituted and that may further include an ether bond, an ester bond, a secondary amino group, a thioether group, or these.

<2> The method for producing a compound represented by general formula (I) according to item <1>, wherein the alkylene group having 2 to 6 carbon atoms in the formula -A$^1$- is preferably formula —(CH$_2$)$_3$— or formula —(CH$_2$)$_4$—.

<3> The method for producing a compound represented by general formula (I) according to item <1> or <2>, wherein the alkylene group having 2 to 6 carbon atoms that may have been substituted in the formula -A$^1$- is preferably an alkylene group having 3 or 4 carbon atoms that may have been substituted.

<4> The method for producing a compound represented by general formula (I) according to any one of items <1> to <3>, wherein the alkylene group having 2 to 6 carbon atoms that may further include an ether bond, an ester bond, a secondary amino group, a thioether group, or these in the formula -A$^1$- is any one of formula —CH$_2$—O—CH$_2$—, formula —CH$_2$—C(=O)—O—CH$_2$—, formula —CH$_2$—NH—CH$_2$—, formula —CH$_2$—S—CH$_2$—, formula —(CH$_2$)$_2$—O—CH$_2$—, formula —(CH$_2$)$_2$—NH—(CH$_2$)$_2$—, formula —(CH$_2$)$_2$—, formula —(CH$_2$)$_3$—, formula —(CH$_2$)$_4$—, formula —(CH$_2$)$_5$—, and formula —(CH$_2$)$_6$—, and is preferably formula —(CH$_2$)$_3$— or formula —(CH$_2$)$_4$—.

<5> The method for producing a compound represented by general formula (I) according to any one of items <1> to <4>, wherein the alkylene group having 4 to 10 carbon atoms in the formula -A$^2$- is preferably formula —(CH$_2$)$_4$—, formula —(CH$_2$)$_6$—, formula —(CH$_2$)$_8$—, or formula —(CH$_2$)$_{10}$—, more preferably formula —(CH$_2$)$_4$—, formula —(CH$_2$)$_6$—, or formula —(CH$_2$)$_{10}$.

<6> The method for producing a compound represented by general formula (I) according to any one of items <1> to <5>, wherein the alkylene group having 4 to 10 carbon atoms that may have been substituted in the formula -A$^2$- is preferably an alkylene group having 4, 6, 8, or 10 carbon atoms, more preferably an alkylene group having 4, 6, or 10 carbon atoms, each of which may have been substituted.

<7> The method for producing a compound represented by general formula (I) according to any one of items <1> to <6>, wherein the alkylene group having 4 to 10 carbon atoms that may further include an ether bond, an ester bond, a secondary amino group, a thioether group, or these in the formula -A$^2$- is any one of formula —(CH$_2$)$_2$—O—(CH$_2$)$_2$—, formula —(CH$_2$)$_2$—NH—(CH$_2$)$_2$—, formula —(CH$_2$)$_4$—, formula —(CH$_2$)$_5$—, formula —(CH$_2$)$_6$—, formula —(CH$_2$)$_7$—, formula —(CH$_2$)$_8$—, formula —(CH$_2$)$_9$—, and formula —(CH$_2$)$_{10}$—, and is preferably formula —(CH$_2$)$_2$—O—(CH$_2$)$_2$—, formula —(CH$_2$)$_4$—, formula —(CH$_2$)$_6$—, formula —(CH$_2$)$_8$—, or formula —(CH$_2$)$_{10}$—, more preferably formula —(CH$_2$)$_4$—, formula —(CH$_2$)$_6$—, or formula —(CH$_2$)$_{10}$—.

<8> The method for producing a compound represented by general formula (I) according to any one of items <1> to <7>, wherein the formula -A$^1$- and the formula -A$^2$- each may have at least one substituent, preferably one or two substituents.

<9> The method for producing a compound represented by general formula (I) according to any one of items <1> to <8>, wherein the substituent is at least one selected from an alkyl group, an alkoxy group, an alkylamino group, an alkoxycarbonyl group, an alkanoyl group, an aryl group, an aralkyl group, an aryloxy group, an acyloxy group, a carboxy group, a halogen atom, a carbon ring, and a heterocyclic ring, and is preferably an alkyl group, an alkoxycarbonyl group, or an alkoxy group, more preferably an alkyl group.

<10> The method for producing a compound represented by general formula (I) according to item <9>, wherein the alkyl group is an alkyl group having 1 to 6 carbon atoms, preferably an alkyl group having 1 to 4 carbon atoms, and more preferably an alkyl group having 1 or 2 carbon atoms.

<11> The method for producing a compound represented by general formula (I) according to item <9>, wherein the alkoxy group is an alkoxy group having 1 to 6 carbon atoms, preferably an alkoxy group having 1 to 4 carbon atoms, and more preferably an alkoxy group having 1 or 2 carbon atoms.

<12> The method for producing a compound represented by general formula (I) according to item <9>, wherein the alkylamino group is an alkylamino group having 1 to 6 carbon atoms, preferably an alkylamino group having 1 to 4 carbon atoms, and more preferably an alkylamino group having 1 or 2 carbon atoms.

<13> The method for producing a compound represented by general formula (I) according to item <9>, wherein the alkoxycarbonyl group is an alkoxycarbonyl group having 1 to 6 carbon atoms in the alkyl moiety, preferably an alkoxycarbonyl group having 1 to 4 carbon atoms in the alkyl moiety, and more preferably an alkoxycarbonyl group having 1 or 2 carbon atoms in the alkyl moiety.

<14> The method for producing a compound represented by general formula (I) according to item <9>, wherein the alkanoyl group is an alkanoyl group having 1 to 6 carbon atoms in the alkyl moiety, preferably an alkanoyl group having 1 to 4 carbon atoms in the alkyl moiety, and more preferably an alkanoyl group having 1 or 2 carbon atoms in the alkyl moiety <15> The method for producing a compound represented by general formula (I) according to item <9>, wherein the aryl group is an aryl group having 6 to 10 carbon atoms.

<16> The method for producing a compound represented by general formula (I) according to item <9>, wherein the aralkyl group is an aralkyl group having 6 to 10 carbon atoms in the aryl moiety and 1 to 6 carbon atoms in the alkyl moiety, preferably an aralkyl group having 6 to 10 carbon atoms in the aryl moiety and 1 to 4 carbon atoms in the alkyl moiety, and more preferably an aralkyl group having 6 to 10 carbon atoms in the aryl moiety and 1 or 2 carbon atoms in the alkyl moiety.

<17> The method for producing a compound represented by general formula (I) according to item <9>, wherein the aryloxy group is an aryloxy group having 6 to 10 carbon atoms.

<18> The method for producing a compound represented by general formula (I) according to item <9>, wherein the acyloxy group is an alkylcarbonyloxy group having 1 to 6 carbon atoms in the alkyl moiety, preferably an alkylcarbonyloxy group having 1 to 4 carbon atoms in the alkyl moiety, and more preferably an alkylcarbonyloxy group having 1 or 2 carbon atoms in the alkyl moiety.

<19> The method for producing a compound represented by general formula (I) according to item <9>, wherein the halogen atom is fluorine, chlorine, bromine, or iodine.

<20> The method for producing a compound represented by general formula (I) according to item <9>, wherein the carbon ring is saturated cyclic hydrocarbon having 3 to 10 carbon atoms or unsaturated cyclic hydrocarbon having 4 to 10 carbon atoms.

<21> The method for producing a compound represented by general formula (I) according to item <9>, wherein the heterocyclic ring is saturated cyclic hydrocarbon having 3 to 10 carbon atoms including a heteroatom or unsaturated cyclic hydrocarbon having 4 to 10 carbon atoms including a heteroatom.

<22> The method for producing a compound represented by general formula (I) according to any one of items <1> to <21>, wherein the formula -$A^1$- is any one of formula —$CH_2$—O—$CH_2$—, formula —$CH_2$—C(=O)—O—$CH_2$—, formula —$CH_2$—NH—$CH_2$—, formula —$CH_2$—S—$CH_2$—, formula —$(CH_2)_2$—O—$CH_2$—, formula —$(CH_2)_2$—NH—$(CH_2)_2$—, formula —$(CH_2)_2$—, formula —$(CH_2)_3$—, formula —$(CH_2)_4$—, formula —$(CH_2)_5$—, and formula —$(CH_2)_6$—, each of which may have been substituted, preferably formula —$(CH_2)_3$— or formula —$(CH_2)_4$—, and more preferably formula —$(CH_2)_3$—, formula —$(CH_2)_4$—, or formula —$CH_2$—CH($CH_3$)$CH_2$—, each of which may have been substituted.

<23> The method for producing a compound represented by general formula (I) according to any one of items <1> to <22>, wherein the formula -$A^2$- is any one of formula —$(CH_2)_2$—O—$(CH_2)_2$—, formula —$(CH_2)_2$—NH—$(CH_2)_2$—, formula —$(CH_2)_4$—, formula —$(CH_2)_5$—, formula —$(CH_2)_6$—, formula —$(CH_2)_7$—, formula —$(CH_2)_8$—, formula —$(CH_2)_9$—, and formula —$(CH_2)_{10}$—, each of which may have been substituted, preferably formula —$(CH_2)_2$—O—$(CH_2)_2$—, formula —$(CH_2)_4$—, formula —$(CH_2)_6$—, formula —$(CH_2)_8$—, or formula —$(CH_2)_{10}$—, more preferably formula —$(CH_2)_2$—O—$(CH_2)_2$—, formula —$(CH_2)_4$—, formula —$(CH_2)_6$—, formula —$(CH_2)_8$—, or formula —$(CH_2)_{10}$—, and further preferably formula —$(CH_2)_4$—, formula —$(CH_2)_6$—, or formula —$(CH_2)_{10}$—, each of which may have been substituted.

<24> The method for producing a compound represented by general formula (I) according to any one of items <1> to <23>, wherein the formula -$A^1$- (where the front bond denotes a bond that bonds with a carbon atom $C^1$ while the back bond denotes a bond that bonds with a carbon atom $C_2$) is preferably an alkylene group having 3 or 4 carbon atoms, more preferably formula —$(CH_2)_3$—, formula —$CH_2$—CH($CH_3$)—$CH_2$—, or formula —$(CH_2)_4$—, and further preferably formula —$CH_2$—CH($CH_3$)—$CH_2$—, each of which may have been substituted.

<25> The method for producing a compound represented by general formula (I) according to any one of items <1> to <24>, wherein the formula -$A^2$- (where the front bond denotes a bond that bonds with a carbon atom $C^1$ while the back bond denotes a bond that bonds with a carbon atom $C^2$) is preferably an alkylene group having 4, 6, 8, or 10 carbon atoms, more preferably formula —$(CH_2)_4$—, formula —$CH_2$—CH($CH_3$)—$CH_2$—$CH_2$—, formula —$CH_2$—$CH_2$—CH($CH_3$—$CH_2$—, formula —$(CH_2)_6$—, formula —$(CH_2)_8$—, or formula —$(CH_2)_{10}$—, further preferably formula —$(CH_2)_4$—, formula —$(CH_2)_6$—, formula —$(CH_2)_8$—, or formula —$(CH_2)_{10}$—, still further preferably formula —$(CH_2)_4$—, formula —$(CH_2)_6$—, or formula —$(CH_2)_{10}$—, and yet further preferably formula —$(CH_2)_{10}$—, each of which may have been substituted.

<26> The method for producing a compound represented by general formula (I) according to any one of items <1> to <25>, wherein the compound represented by general formula (II) is preferably a compound represented by formula (i), a compound represented by formula (iii), a compound represented by formula (vii), or a compound represented by formula (viii), more preferably a compound represented by formula (vii).

<27> The method for producing a compound represented by general formula (I) according to any one of items <1> to <26>, wherein the acid catalyst is at least one of Bronsted acid and Lewis acid.

<28> The method for producing a compound represented by general formula (I) according to item <27>, wherein the Bronsted acid is a Bronsted acid having a pKa (in water) of not more than 2.0, preferably sulfuric acid (pKa=1.96), phosphoric acid (pKa=1.83), trifluoroacetic acid (pKa=−0.3), or p-toluenesulfonic acid (pKa=−2.8).

<29> The method for producing a compound represented by general formula (I) according to item <27>, wherein the Lewis acid is metal chloride or metal triflate.

<30> The method for producing a compound represented by general formula (I) according to item <29>, wherein the metal chloride is any one of molybdenum chloride, tungsten chloride, aluminum chloride, and tin chloride.

<31> The method for producing a compound represented by general formula (I) according to item <29>, wherein the metal triflate is either indium triflate or scandium triflate.

<32> The method for producing a compound represented by general formula (I) according to item <27>, wherein the Bronsted acid is a Bronsted acid having a pKa (in water) of not more than 2.0, preferably sulfuric acid, phosphoric acid, trifluoroacetic acid, or p-toluenesulfonic acid.

<33> The method for producing a compound represented by general formula (I) according to any one of items <1> to <32>, wherein the tungstic acid compound is any one of tungstic acid, isopolytungstic acid, and heteropolytungstic acid, preferably tungstic acid.

<34> The method for producing a compound represented by general formula (I) according to item <33>, wherein the tungstic acid is any one of orthotungstic acid ($H_2WO_4$), metatungstic acid ($H_6[H_2W_{12}O_{40}]$), paratungstic acid ($H_6[H_{10}W_{12}O_{46}]$), and phosphotungstic acid ($H_3PW_{12}O_{40}$ (n$H_2$O)), preferably orthotungstic acid ($H_2WO_4$).

<35> The method for producing a compound represented by general formula (I) according to any one of items <1> to <34>, wherein the acid catalyst and the tungstic acid compound are preferably at least one of a Bronsted acid having a pKa of not more than 2.0 and a tungstic acid compound, more preferably tungstic acid, and further preferably orthotungstic acid.

<36> The method for producing a compound represented by general formula (I) according to any one of items <1> to <35>, wherein the molar ratio of the compound of formula (II) to the acid catalyst (the compound of formula (II): the acid catalyst) is preferably 1:0.001 to 1:0.7, more preferably 1:0.005 to 1:0.5, and further preferably 1:0.01 to 1:0.3.

<37> The method for producing a compound represented by general formula (I) according to any one of items <1> to <36>, wherein the molar ratio of the compound of formula (II) to the tungstic acid compound (the compound of formula (II): the tungstic acid compound) is preferably 1:0.001 to 1:0.7, more preferably 1:0.005 to 1:0.5, and further preferably 1:0.01 to 1:0.3.

<38> The method for producing a compound represented by general formula (I) according to any one of items <1> to <37>, wherein the molar ratio of the compound of formula (II) to the hydrogen peroxide (the compound of formula (II): the hydrogen peroxide) is preferably 1:10 to 1:2, more preferably 1:7 to 1:2, and further preferably 1:5 to 1:2.5.

<39> The method for producing a compound represented by general formula (I) according to any one of items <1> to <38>, wherein the oxidative cleavage is carried out at a temperature preferably between 0° C. and 100° C., more preferably at 20° C. or higher, further preferably at 80° C. or lower, and still further preferably at 50° C. or lower.

<40> The method for producing a compound represented by general formula (I) according to any one of items <1> to <39>, wherein the compound represented by general formula (II) is 14-methylbicyclo[10.3.0]pentadecene[1(12)], and the compound represented by general formula (I) is 3-methyl-1,5-cyclopentadecanedione.

<41> A method for producing a cyclic ketone compound represented by formula (3), the method including:
obtaining 3-methyl-1,5-cyclopentadecanedione by a method according to item <40>; and
a step (a) of partially reducing the 3-methyl-1,5-cyclopentadecanedione and then dehydrating it to obtain the cyclic ketone compound represented by formula (3) or a step (b) of reducing the 3-methyl-1,5-cyclopentadecanedione, then enoletherifying it, and subsequently decyclizing it to obtain the cyclic ketone compound represented by formula (3).

[Chemical Formula 12]

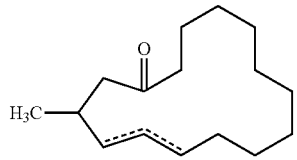

(3)

<42> The method for producing a cyclic ketone compound represented by formula (3) according to item <41>, wherein the step (a) includes:
a step (a-1) of partially reducing the 3-methyl-1,5-cyclopentadecanedione (1) to obtain 3-methylcyclopentadecanol-5-one (2); and
a step (a-2) of dehydrating the 3-methylcyclopentadecanol-5-one (2) to obtain the cyclic ketone compound represented by formula (3).

<43> The method for producing a cyclic ketone compound represented by formula (3) according to item <42>, wherein the method for partially reducing the 3-methyl-1,5-cyclopentadecanedione (1) in the step (a-1) is preferably a method in which metal hydride (for example, sodium borohydride or sodium hydride) is used or a method in which hydrogenation is carried out in the presence of a metal catalyst (for example, palladium carbon or Raney nickel, preferably Raney nickel), more preferably the method in which hydrogenation is carried out in the presence of a metal catalyst.

<44> The method for producing a cyclic ketone compound represented by formula (3) according to item <43>, wherein the method for partially reducing the 3-methyl-1,5-cyclopentadecanedione (1) in the step (a-1) is the method in which hydrogenation is carried out in the presence of a metal catalyst, and the amount of the metal catalyst to be used with respect to the 3-methyl-1,5-cyclopentadecanedione (1) is preferably 1:0.01 to 1:1, more preferably 1:0.1 to 1:0.5, in terms of molar ratio of the 3-methyl-1,5-cyclopentadecanedione (1) to the metal catalyst (the 3-methyl-1,5-cyclopentadecanedione (1): the metal catalyst).

<45> The method for producing a cyclic ketone compound represented by formula (3) according to item <43> or <44>, wherein the method for partially reducing the 3-methyl-1,5-cyclopentadecanedione (1) in the step (a-1) is the method in which hydrogenation is carried out in the presence of a metal catalyst, and the hydrogen pressure for the hydrogenation is preferably at least 0.1 MPa but is preferably not higher than 2.0 MPa, more preferably not higher than 1.0 MPa.

<46> The method for producing a cyclic ketone compound represented by formula (3) according to any one of items <42> to <45>, wherein the method for dehydrating the 3-methylcyclopentadecanol-5-one (2) in the step (a-2) is a method for dehydrating it in the presence of acid (for example, sulfuric acid, phosphoric acid, or benzenesulfonic acid, preferably benzenesulfonic acid).

<47> The method for producing a cyclic ketone compound represented by formula (3) according to item <41>, wherein the step (b) includes:
a step (b-1) of reducing the 3-methyl-1,5-cyclopentadecanedione (1) to obtain 3-methylcyclopentadecane-1,5-diol (4);
a step (b-2) of partially oxidizing and enoletherifying the 3-methylcyclopentadecane-1,5-diol (4) to obtain 16-oxa-3-methylbicyclo[10.3.1]pentadec-1-en (5); and
a step (b-3) of decyclizing the 16-oxa-3-methylbicyclo[10.3.1]pentadec-1-en (5) to obtain the cyclic ketone compound represented by formula (3).

<48> The method for producing a cyclic ketone compound represented by formula (3) according to item <47>, wherein the method for partially reducing the 3-methyl-1,5-cyclopentadecanedione (1) in the step (b-1) is carried out preferably by a method in which metal hydride (for example, sodium borohydride or sodium hydride) is used or a method in which hydrogenation is carried out in the presence of a metal catalyst (for example, palladium carbon or Raney nickel, preferably Raney nickel), more preferably by the method in which hydrogenation is carried out in the presence of a metal catalyst.

<49> The method for producing a cyclic ketone compound represented by formula (3) according to item <48>, wherein the method for partially reducing the 3-methyl-1,5-cyclopentadecanedione (1) in the step (b-1) is the method in which hydrogenation is carried out in the presence of a metal catalyst, and the hydrogen pressure for the hydrogenation is preferably at least 0.1 MPa but is preferably not higher than 2.0 MPa, more preferably not higher than 1.0 MPa.

<50> The method for producing a cyclic ketone compound represented by formula (3) according to any one of items <47> to <49>, wherein the method for partially oxidizing and enoletherifying the 3-methylcyclopentadecane-1,5-diol (4) in the step (b-2) is a method for partially oxidizing and enoletherifying it in the presence of a metal catalyst (for example, a metal catalyst having oxidizability, preferably aluminum oxide, iron oxide, Raney copper, etc., more preferably Raney copper).

<51> The method for producing a cyclic ketone compound represented by formula (3) according to item <50>, wherein the molar ratio of the 3-methylcyclopentadecane-1,5-diol (4) to the metal catalyst (the 3-methylcyclopentadecane-1,5-diol (4): the metal catalyst) is preferably 1:0.01 to 1:1, more preferably 1:0.05 to 1:0.3.

<52> The method for producing a cyclic ketone compound represented by formula (3) according to any one of items <47> to <51>, wherein the method for decyclizing the 16-oxa-3-methylbicyclo[10.3.1]pentadec-1-en (5) in the step (b-3) is a method for decyclizing it in the presence of acid (for example, sulfuric acid, phosphoric acid, or benzenesulfonic acid, preferably phosphoric acid).

<53> The method for producing a cyclic ketone compound represented by formula (3) according to item <52>, wherein the molar ratio of the 16-oxa-3-methylbicyclo[10.3.1]pentadec-1-en (5) to the acid (the 16-oxa-3-methylbicyclo[10.3.1]pentadec-1-en (5): the acid) is preferably 1:0.01 to 1:1, more preferably 1:0.1 to 1:0.5.

EXAMPLES

[Yield of Compound]

The yield of each compound obtained in the examples was calculated by measuring the mass of the compound contained in a crude product by gas chromatography internal standard quantitative analysis, and dividing the number of moles of said compound by the number of moles of raw materials.

<Apparatus and Analytical Conditions for Gas Chromatography>
GC Apparatus: Manufactured by HEWLET PACKARD, Type: HP6850
Column: Manufactured by J&W, DB-1 (inner diameter: 0.25 mm, length: 30 m, and film thickness: 0.25 μm)
Carrier Gas: He, 1.5 mL/min
Injection Condition: 300° C., split ratio: 1/100
Detection Condition: FID System, 300° C.
Column Temperature Condition: 80° C.→raising the temperature at 10° C./min→300° C. maintained for 10 minutes
Internal Standard Compound: n-tridecane

[Identification of Compound]

Each compound obtained in the following examples and comparative examples was identified by spectrum analysis using a gas chromatography mass spectrometer (GC-MS, manufactured by Shimadzu Corporation, Type: GC-2010).
<Apparatus and Analytical Conditions for GC-MS>
GC Apparatus: Manufactured by Shimadzu Corporation, Type: GC-2010
MS Apparatus: Manufactured by Shimadzu Corporation, Type: GCMS-QP2010 Plus
Column: Manufactured by J&W, DB-1 (inner diameter: 0.25 mm, length: 30 m, and film thickness: 0.25 μm)
Carrier Gas: He, 1.8 mL/min
Injection Condition: 300° C., split ratio: 1/50
Detection Condition: FID System, 250° C.
Column Temperature Condition: 90° C.→raising the temperature at 5° C./min→150° C.→raising the temperature at 10° C./min→250° C. maintained for 28 minutes
Ion Source Temperature: 200° C.

Example 1

0.2425 g (2.5 mmol) of 35% by mass hydrogen peroxide solution was added to 0.0124 g (0.05 mmol) of orthotungstic acid ($H_2WO_4$). This was stirred at 20° C. for 20 minutes. Then 3.9 g of t-butyl alcohol and 0.22 g (1.0 mmol) of 14-methylbicyclo[10.3.0]pentadecene[1(12)] were added to the mixture. This was stirred at a reaction temperature of 40° C. for 80 hours. After the completion of the reaction, 10 ml of 10% by mass sodium sulfite aqueous solution was added to the mixture in an ice bath and thus it was quenched. Thereafter, an organic layer was extracted from the mixture using 30 ml of diethyl ether. Then after being dried with magnesium sulfate, the organic layer was filtrated. Thereafter, the solvent was removed from the filtrate under reduced pressure, and thus 0.3 g of crude product was obtained. The 3-methyl-1,5-cyclopentadecanedione (the compound of formula (1)) contained in the crude product had a yield of 77.9%. The reaction formula is shown below.

Furthermore, the results of the measurement of the 3-methyl-1,5-cyclopentadecanedione (the compound of formula (1)) by gas chromatography mass spectrometry (GC-MS) are indicated below. In the below, the numerical values in the parentheses each indicate the relative intensity of each spectrum.

MS: 252 (22, M+), 209 (12), 195 (28), 142 (22), 139 (16), 97 (60), 85 (62), 69 (100), 55 (62)

[Chemical Formula 13]

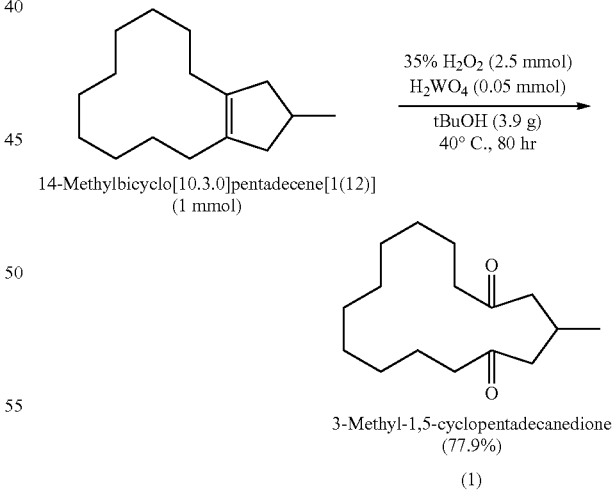

Examples 2 to 13

For producing the 3-methyl-1,5-cyclopentadecanedione (the compound of formula (1)), the reaction was carried out in the same manner as in Example 1 except that the conditions were changed as indicated in Table 1. The results are indicated in Table 1.

TABLE 1

| Example | 35% by mass Hydrogen Peroxide Solution | Tungstic Acid Compound or Acid Catalyst | Reaction Solvent | Reaction Temperature | Reaction Time | Yield of Compound of Formula (1) |
|---|---|---|---|---|---|---|
| Ex. 2 | 35 wt % H$_2$O$_2$ (4 mmol) | H$_3$PW$_{12}$O$_{40}$(nH$_2$O) (0.2 mmol) | tBuOH (3.9 g) | 100° C. | 18 hr | 13.6% |
| Ex. 3 | 35 wt % H$_2$O$_2$ (4.5 mmol) | Na$_2$WO$_4$ (0.1 mmol) | tBuOH (3.9 g) | 90° C. | 21 hr | 6.8% |
| Ex. 4 | 35 wt % H$_2$O$_2$ (5 mmol) | H$_2$WO$_4$ (0.2 mmol) | tBuOH (3.9 g) | 20° C. | 165 hr | 43.6% |
| Ex. 5 | 35 wt % H$_2$O$_2$ (7 mmol) | H$_2$WO$_4$ (0.5 mmol) | tBuOH (3.9 g) | 20° C. | 284 hr | 53.4% |
| Ex. 6 | 35 wt % H$_2$O$_2$ (2.5 mmol) | H$_2$WO$_4$ (0.2 mmol) | tBuOH (3.9 g) | 40° C. | 56 hr | 70.2% |
| Ex. 7 | 35 wt % H$_2$O$_2$ (2.5 mmol) | H$_2$WO$_4$ (0.1 mmol) | tBuOH (3.9 g) | 40° C. | 95 hr | 78.6% |
| Ex. 8 | 35 wt % H$_2$O$_2$ (2.5 mmol) | H$_2$WO$_4$ (0.01 mmol) | tBuOH (3.9 g) | 40° C. | 64 hr | 69.9% |
| Ex. 9 | 35 wt % H$_2$O$_2$ (2.5 mmol) | CF$_3$COOH (0.2 mmol) | tBuOH (0.78 g) | 40° C. | 46 hr | 20.0% |
| Ex. 10 | 35 wt % H$_2$O$_2$ (2.5 mmol) | H$_3$PO$_4$ (0.2 mmol) | tBuOH (0.78 g) | 40° C. | 46 hr | 15.0% |
| Ex. 11 | 35 wt % H$_2$O$_2$ (2.5 mmol) | CF$_3$SO$_3$H (0.05 mmol) | tBuOH (0.78 g) | 20° C. | 8 hr | 10.0% |
| Ex. 12 | 35 wt % H$_2$O$_2$ (2.5 mmol) | H$_2$WO$_4$ (0.05 mmol) | EtOH (0.78 g) | 40° C. | 17 hr | 16.3% |
| Ex. 13 | 35 wt % H$_2$O$_2$ (2.5 mmol) | H$_2$WO$_4$ (0.05 mmol) | iPrOH (0.78 g) | 40° C. | 15 hr | 18.6% |

Based on the results indicated in Table 1, it was confirmed that according to the method of the present disclosure, the compound of formula (I) can be produced using hydrogen peroxide in the presence of an acid catalyst or in the presence of a tungstic acid compound.

Examples 14 and 15

The reaction was carried out in the same manner as in Example 1 except that each compound of formula (II) indicated in Table 2 was used instead of the 14-methylbicyclo[10.3.0]pentadecene[1(12)]. The results are indicated in Table 2.

TABLE 2

| Example | Compound of Formula (II) | Reaction Time | Target | Yield of Target |
|---|---|---|---|---|
| Ex. 14 | 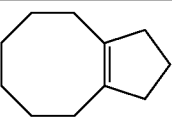 [SMILES: C1CCCC2=C(CC1)CCC2] | 100 hr | 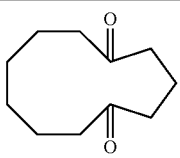 [SMILES: O=C1CCCCCCC(=O)CCC1] | 5.0% |

TABLE 2-continued

| Example | Compound of Formula (II) | Reaction Time | Target | Yield of Target |
|---|---|---|---|---|
| Ex. 15 | (bicyclic structure) | 28 hr | (cyclic diketone structure) | 12.0% |

Based on the results indicated in Table 2, it was confirmed that according to the method of the present disclosure, the compound of formula (I) can be produced using hydrogen peroxide in the presence of a tungstic acid compound.

<Production of Cyclic Ketone Compound Represented by Formula (3)>

Example 16

[Chemical Formula 14]

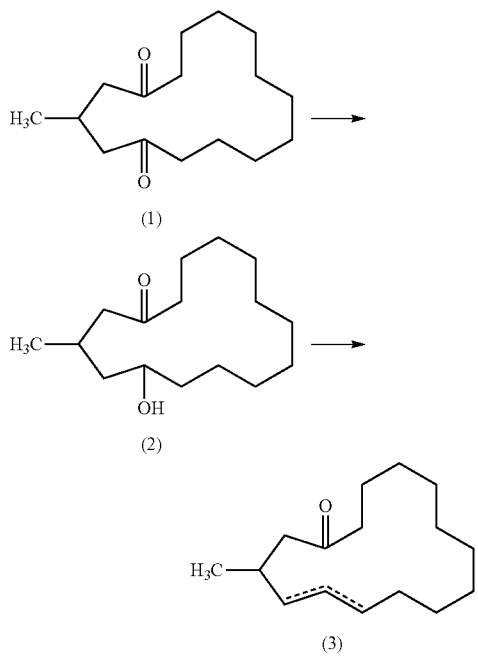

3 ml of methanol, 0.06 g (0.1 mmol) of Raney nickel catalyst, which was 10% by mass alcoholic suspension, and 0.03 ml of 10% by mass aqueous sodium hydroxide solution were added to 0.15 g (0.594 mmol) of 3-methyl-1,5-cyclopentadecanedione (the compound of formula (1)) obtained in Example 1. Thereafter, it was stirred in hydrogen at room temperature (25° C.) and normal pressure (0.1 MPa) for 45 minutes, and then from the filtrate obtained by filtration thereof the solvent was removed under reduced pressure. The residue was diluted with diethyl ether and then was washed with 10% by mass aqueous sodium bicarbonate solution and water. After the organic layer was extracted, it was dried with magnesium sulfate and then filtrated. Thereafter, the solvent was removed from the filtrate under reduced pressure, and thus 0.2 g of crude product was obtained. The crude product was analyzed by gas chromatography and the resultant 3-methylcyclopentadecanol-5-one (the compound of formula (2)) had a yield of 50.0%.

3 ml of toluene and 0.004 g (0.027 mmol) of benzenesulfonic acid were added to 0.07 g (0.275 mmol) of 3-methylcyclopentadecanol-5-one (the compound of formula (2)). This was stirred under heating and reflux (110° C.) for one hour. Thereafter, 10% by mass aqueous sodium bicarbonate solution was added thereto at room temperature (25° C.). After the organic layer was extracted, it was dried with magnesium sulfate and then filtrated. Thereafter, the solvent was removed from the filtrate under reduced pressure, and thus 0.06 g of crude product was obtained. The crude product was analyzed by gas chromatography and the resultant cyclic ketone compound represented by formula (3) had a yield of 80.0%.

Example 17

[Chemical Formula 15]

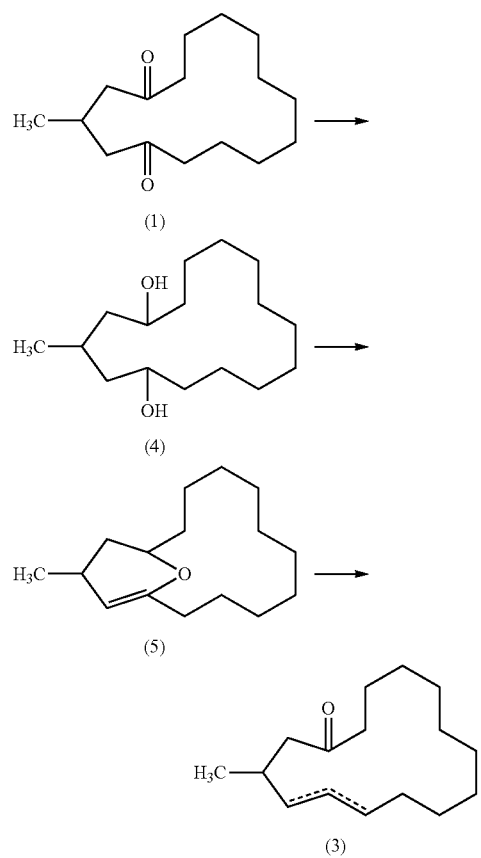

3 ml of methanol, 0.06 g (0.1 mmol) of Raney nickel catalyst, which was 10% by mass alcoholic suspension, and 0.03 ml of 10% by mass aqueous sodium hydroxide solution were added to 0.15 g (0.594 mmol) of 3-methyl-1,5-cyclopentadecanedione (the compound of formula (1)) obtained in Example 1. Thereafter, it was stirred in hydrogen at room temperature (25° C.) and normal pressure (0.1 MPa) for 24 hours, and then from the filtrate obtained by filtration thereof, the solvent was removed under reduced pressure. The residue was diluted with diethyl ether and then was washed with 10% by mass aqueous sodium bicarbonate solution and water. After the organic layer was extracted, it was dried with magnesium sulfate and then filtrated. Thereafter, the solvent was removed from the filtrate under reduced pressure, and thus 0.2 g of crude product was obtained. The crude product was analyzed by gas chromatography and the resultant 3-methylcyclopentadecane-1,5-diol (the compound of formula (4)) had a yield of 80.0%.

0.06 g (0.09 mmol) of Raney copper, which was 10% by mass aqueous suspension, was added to 0.12 g (0.46 mmol) of 3-methylcyclopentadecane-1,5-diol (the compound of formula (4)). This was stirred under reduced pressure of 45 mmHg at 165° C. for three hours. Thereafter, it was distilled under reduced pressure of 2 mmHg and as a result, 0.06 g of distillate fraction was obtained. The distillate fraction was analyzed by gas chromatography. The resultant 16-oxa-3-methylbicyclo[10.3.1]pentadec-1-ene (the compound of formula (5)) had a yield of 50.0%.

1 ml of toluene and 0.01 g (0.08 mmol) of 80% by mass aqueous phosphoric acid solution were added to 0.05 g (0.21 mmol) of 16-oxa-3-methylbicyclo[10.3.1]pentadec-1-ene (the compound of formula (5)). This was stirred under heating and reflux (110° C.) for three hours while water that had been by-produced was removed continuously. After being cooled, it was washed with water and 10% by mass aqueous sodium carbonate solution. The organic layer was extracted and then the solvent was removed under reduced pressure. Thus 0.05 g of crude product was obtained. The crude product was analyzed by gas chromatography, and the resultant cyclic ketone compound represented by formula (3) had a yield of 85.0%.

Comparative Example

The reaction was carried out in the same manner as in Example 1 except that 1,2-dimethylcyclododec-1-ene was used instead of the 14-methylbicyclo[10.3.0]pentadecene[1(12)]. As a result, tetradecane-2,13-dione, which is obtained by oxidative cleavage of 1,2-dimethylcyclododec-1-ene, was not obtained.

[Chemical Formula 16]

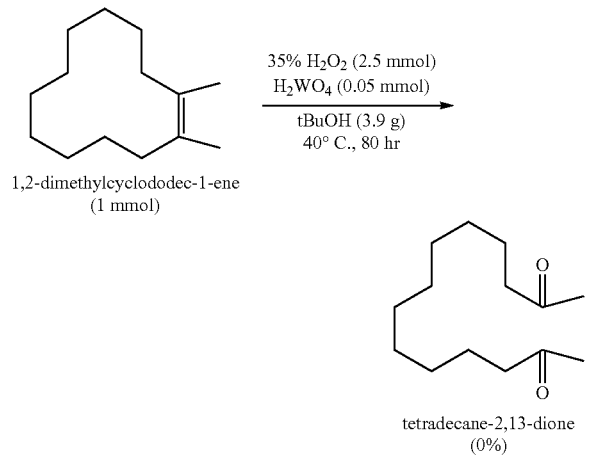

Based on the result of the comparative example, it was confirmed that the monocyclic tetrasubstituted olefin compound cannot be subjected to oxidative cleavage using hydrogen peroxide in the presence of a tungstic acid compound.

INDUSTRIAL APPLICABILITY

According to the production method of the present disclosure, a compound represented by general formula (I) can be produced by oxidative cleavage of a compound of formula (II), which is a bicyclic tetrasubstituted olefin compound, using hydrogen peroxide in the presence of an acid catalyst or in the presence of a tungstic acid compound. The production method of the present disclosure uses hydrogen peroxide and thereby provides the effects of being highly versatile, safe, and harmless to the environment.

The invention claimed is:

1. A method for producing a compound represented by general formula (I), the method comprising:
    subjecting a compound represented by general formula (II) to oxidative cleavage using hydrogen peroxide in the presence of an acid catalyst or in the presence of a tungstic acid compound, wherein the acid catalyst is a Bronsted acid having a pKa (in water) of not more than 2.0, to obtain the compound represented by general formula (I):

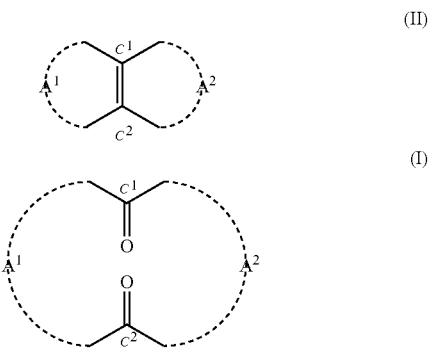

wherein
    $A^1$ bonds in a first $A^1$ bond with a carbon atom $C^1$ and bonds in a second $A^1$ bond with a carbon atom $C^2$,
    $A^1$ is an alkylene group having 2 to 6 carbon atoms that is optionally substituted and that optionally further comprises an ether bond, an ester bond, a secondary amino group, a thioether group, or a combination thereof,
    $A^2$ bonds in a first $A^2$ bond with a carbon atom $C^1$ and bonds in a second $A^2$ bond with a carbon atom $C^2$,
    $A^2$ is an alkylene group having 4 to 10 carbon atoms that is optionally substituted and that optionally further comprises an ether bond, an ester bond, a secondary amino group, a thioether group, or a combination thereof.

2. The method for producing a compound represented by general formula (I) according to claim 1, wherein
    $A^1$ is an alkylene group having 3 or 4 carbon atoms that is optionally substituted, and
    $A^2$ is an alkylene group having 4, 6, 8, or 10 carbon atoms that m is optionally substituted.

3. The method for producing a compound represented by general formula (I) according to claim 1, wherein
    the oxidative cleavage is in the presence of the acid catalyst.

4. The method for producing a compound represented by general formula (I) according to claim 1, wherein
    the Bronsted acid is sulfuric acid, phosphoric acid, trifluoroacetic acid, or p-toluenesulfonic acid.

5. The method for producing a compound represented by general formula (I) according to claim 1, wherein
the oxidative cleavage is in the presence of the tungstic acid compound, which is tungstic acid, isopolytungstic acid, or heteropolytungstic acid.

6. The method for producing a compound represented by general formula (I) according to claim 5, wherein
the tungstic acid is orthotungstic acid ($H_2WO_4$), metatungstic acid ($H_6[H_2W_{12}O_{40}]$), paratungstic acid ($H_6[H_{10}W_{12}O_{46}]$), or phosphotungstic acid ($H_3PW_{12}O_{40}$ ($nH_2O$)).

7. The method for producing a compound represented by general formula (I) according to claim 6, wherein
the tungstic acid compound is orthotungstic acid ($H_2WO_4$).

8. The method for producing a compound represented by general formula (I) according to claim 1, wherein
the oxidative cleavage is in the presence of the acid catalyst, and
the molar ratio of the compound of formula (II) to the acid catalyst (the compound of formula (II): the acid catalyst) is 1:0.001 to 1:0.7.

9. The method for producing a compound represented by general formula (I) according to claim 1, wherein
the oxidative cleavage is in the presence of the tungstic acid compound, and
the molar ratio of the compound of formula (II) to the tungstic acid compound (the compound of formula (II): the tungstic acid compound) is 1:0.001 to 1:0.7.

10. The method for producing a compound represented by general formula (I) according to claim 1, wherein
the molar ratio of the compound of formula (II) to the hydrogen peroxide (the compound of formula (II): the hydrogen peroxide) is 1:10 to 1:2.

11. The method for producing a compound represented by general formula (I) according to claim 1, wherein
the compound represented by general formula (II) is 14-methylbicyclo[10.3.0]pentadecene[1(12)], and the compound represented by general formula (I) is 3-methyl-1,5-cyclopentadecanedione.

12. A method for producing a cyclic ketone compound represented by formula (3):

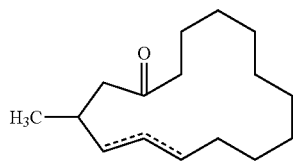

(3)

the method comprising:
obtaining 3-methyl-1,5-cyclopentadecanedione by the method according to claim 11; and
(a) partially reducing the 3-methyl-1,5-cyclopentadecanedione and then dehydrating it to obtain the cyclic ketone compound represented by formula (3) or (b) reducing the 3-methyl-1,5-cyclopentadecanedione, then enoletherifying it, and subsequently decyclizing it to obtain the cyclic ketone compound represented by formula (3).

13. The method for producing a compound represented by general formula (I) according to claim 1, wherein $A^2$ is
—$(CH_2)_2$—O—$(CH_2)_2$—, —$(CH_2)_4$—, —$(CH_2)_6$—, —$(CH_2)_8$—, or —$(CH_2)_{10}$—, each of which is optionally substituted.

14. The method for producing a compound represented by general formula (I) according to claim 1, wherein $A^2$ is
—$(CH_2)_4$—, —$(CH_2)_6$—, or —$(CH_2)_{10}$—.

15. The method for producing a compound represented by general formula (I) according to claim 1, wherein the oxidative cleavage is in the presence of the acid catalyst, and wherein the molar ratio of the compound of formula (II) to the acid catalyst (the compound of formula (II): the acid catalyst) is 1:0.005 to 1:0.5.

16. The method for producing a compound represented by general formula (I) according to claim 1, wherein the oxidative cleavage is in the presence of the tungstic acid compound, and wherein the molar ratio of the compound of formula (II) to the tungstic acid compound (the compound of formula (II): the tungstic acid compound) is 1:0.005 to 1:0.5.

17. The method for producing a compound represented by general formula (I) according to claim 1, wherein the molar ratio of the compound of formula (II) to the hydrogen peroxide (the compound of formula (II): the hydrogen peroxide) is 1:7 to 1:2.

18. The method for producing a cyclic ketone compound represented by formula (3) according to claim 12, the process comprising (a) partially reducing the 3-methyl-1,5-cyclopentadecanedione and then dehydrating it to obtain the cyclic ketone compound represented by formula (3), wherein (a) comprises:
(a-1) partially reducing the 3-methyl-1,5-cyclopentadecanedione (1) to obtain 3-methylcyclopentadecanol-5-one (2); and
(a-2) dehydrating the 3-methylcyclopentadecanol-5-one (2) to obtain the cyclic ketone compound represented by formula (3).

19. The method for producing a cyclic ketone compound represented by formula (3) according to claim 12, the process comprising (b) reducing the 3-methyl-1,5-cyclopentadecanedione, then enoletherifying it, and subsequently decyclizing it to obtain the cyclic ketone compound represented by formula (3), wherein (b) comprises:
(b-1) reducing the 3-methyl-1,5-cyclopentadecanedione (1) to obtain 3-methylcyclopentadecane-1,5-diol (4);
(b-2) partially oxidizing and enoletherifying the 3-methylcyclopentadecane-1,5-diol (4) to obtain 16-oxa-3-methylbicyclo[10.3.1]pentadec-1-en (5); and
(b-3) decyclizing the 16-oxa-3-methylbicyclo[10.3.1]pentadec-1-en (5) to obtain the cyclic ketone compound represented by formula (3).

* * * * *